(12) United States Patent
Cho et al.

(10) Patent No.: US 9,056,041 B2
(45) Date of Patent: Jun. 16, 2015

(54) C-SPINE HEAD STABILIZATION DEVICE

(71) Applicants: David Colin Cho, Honolulu, HI (US); Allen Gabriel, Camas, WA (US); Wil Kazuo Yamamoto, Honolulu, HI (US)

(72) Inventors: David Colin Cho, Honolulu, HI (US); Allen Gabriel, Camas, WA (US); Wil Kazuo Yamamoto, Honolulu, HI (US)

( * ) Notice: Subject to any disclaimer, the term of this patent is extended or adjusted under 35 U.S.C. 154(b) by 0 days.

(21) Appl. No.: 14/020,455

(22) Filed: Sep. 6, 2013

(65) Prior Publication Data
US 2014/0076331 A1    Mar. 20, 2014

Related U.S. Application Data

(60) Provisional application No. 61/701,691, filed on Sep. 16, 2013.

(51) Int. Cl.
| | |
|---|---|
| *A61G 13/12* | (2006.01) |
| *A61F 5/05* | (2006.01) |
| *A61F 5/04* | (2006.01) |
| *A61F 5/058* | (2006.01) |
| *A61F 5/055* | (2006.01) |

(52) U.S. Cl.
CPC .............. *A61G 13/121* (2013.01); *A61G 13/12* (2013.01); *A61F 5/04* (2013.01); *A61F 5/055* (2013.01); *A61F 5/05883* (2013.01); *A61F 5/05891* (2013.01)

(58) Field of Classification Search
CPC ........ A61G 13/12; A61G 13/121; A61F 5/04; A61F 5/055; A61F 5/05883; A61F 5/05891; B60N 2/02; B60N 2/04; B60N 2/06; B60N 2/07
USPC ............ 128/845, 870; 602/17, 18, 32, 33, 35, 602/36; 5/621, 622, 636, 637; 248/424, 248/429, 430
See application file for complete search history.

(56) References Cited

U.S. PATENT DOCUMENTS

| | | | |
|---|---|---|---|
| 4,400,820 A * | 8/1983 | O'Dell et al. .................. | 378/209 |
| 2012/0124747 A1* | 5/2012 | Soto et al. ......................... | 5/622 |

* cited by examiner

*Primary Examiner* — Alireza Nia
*Assistant Examiner* — Keri J Nelson
(74) *Attorney, Agent, or Firm* — Keri Ann K. S. Krzykowski; Martin E. Hsia

(57) ABSTRACT

The present invention is a device that is configured to secure a patient's head against the force of gravity during surgery (or other medical procedures) while the patient is in an upright, sideways (tilted to the side), or upside down position, or in any other non-horizontal position, for any duration of time. The device is designed to safely secure a patient's head or neck to prevent potential injury to the patient who is unconscious and unable to protect themselves through reflex reactions or otherwise. Without the device, a patient's head would drop forward or sideways by force of gravity, and if it remained in the dropped position, the patient's neck, shoulder, and/or spine regions could suffer temporary or permanent soreness, strain, and/or injury. This device is designed to reduce or eliminate such soreness or injury.

3 Claims, 2 Drawing Sheets

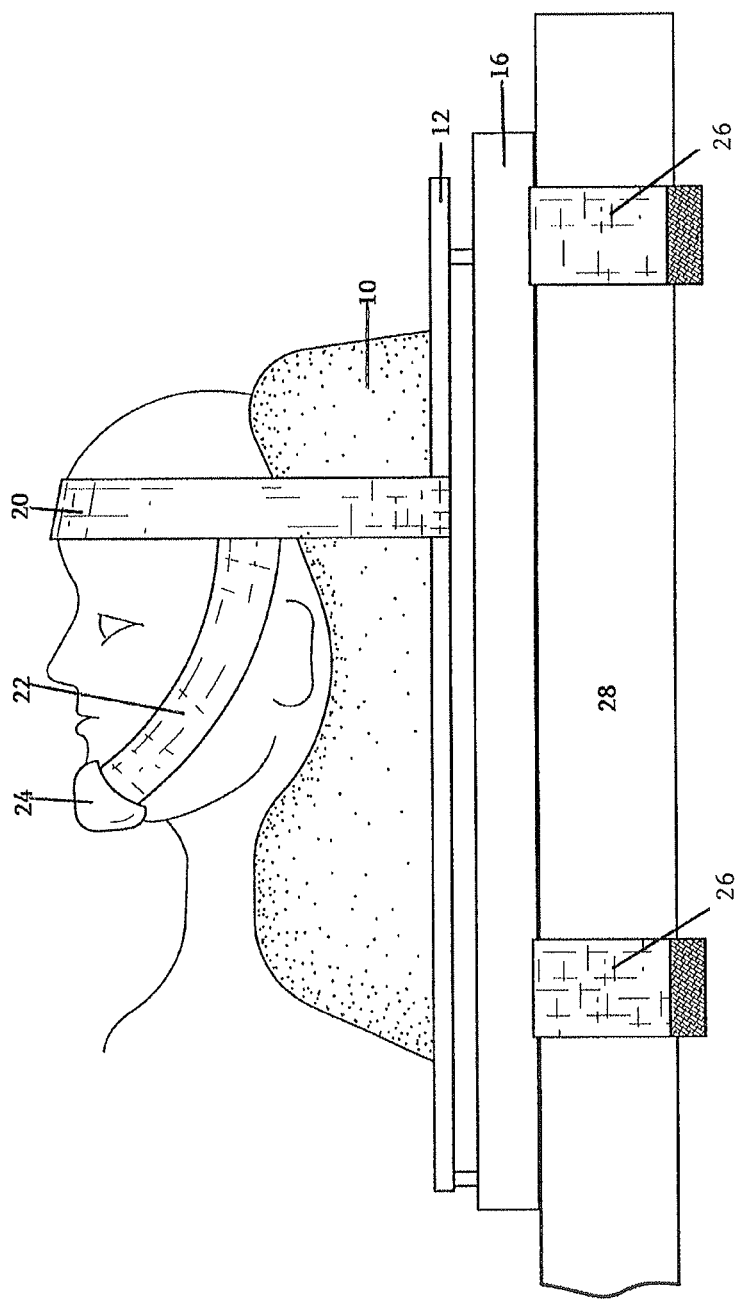

C-SPINE HEAD STABILIZATION DEVICE

This application claims the priority of U.S. provisional patent application No. 61/701,691 filed on Sep. 16, 2012.

TECHNICAL FIELD

The present invention generally relates to head stabilization devices suitable for medical procedures. Specifically, the present invention is a head stabilization device that addresses clinical problems encountered during surgery (or other medical procedures) where a patient is unconscious (or heavily sedated) while being retained in a position that is not supine, but rather upright, sideways, upside down, or in any other position that is at an angle greater than horizontal, on an operating table or some other apparatus.

BACKGROUND ART

Surgery is conventionally performed while a patient is lying in a supine position. Increasingly, surgical procedures (and other medical procedures) require patients to be unconscious and in upright, sideways, or upside down positions, or in some other non-horizontal position. For example, it is preferred for patients to be in an upright position during breast augmentation surgery so that the surgeon can see the full effects of gravity on a patient's breasts for optimum results. However, having the patient in an upright position causes the patient's head and neck to drop forward or sideways by force of gravity. This can lead to soreness and strain on the neck, shoulder, and/or spine region, post-surgery. Clinical documentation of complaints of such soreness resulting from a non-stabilized head during such procedures is increasing. See Hindman B, Palecek J, Posner K, Traynelis V, Lee L, Sawin P, Tredway T, Todd M, Domino K: *Cervical Spinal Cord, Root, and Bony Spine Injuries, A Closed Claims Analysis*. Anesthesiology 2011; 114:782-95; Lanier W, Warner M: *New Perioperative Cervical Injury, Medical and Legal Implications of Patients and Anesthesia Providers*. Anesthesiology 2011; 114:729-31; Dippmann C, Winge S, Nielsen H: *Severe Cerebral Desaturation During Shoulder Arthroscopy in the Beach-Chair Position*. Arthroscopy: The Journal of Arthroscopic and Related Surgery 2010, V26, No. 29, pp. S148-S150; Lee M, Cassinelli E, Riew K: *Prevalence of Cervical Spine Stenosis, Anatomic Study in Cadavers*. The Journal of Bone & Joint Surgery 2007, V89-A, No. 2, pp. 376-80; and Wilder B: *Hypothesis: The Etiology of Midcervical Quadriplegia after Operation with the Patient in the Sitting Position*, Neurosurgery 1982, V11, No. 4, pp. 530-31; (6) Pohl A, Cullen D: *Cerebral ischemia during shoulder surgery in the upright position: a case series*, Journal of Clinical Anesthesia 2005, V17, 463-469, incorporated herein by reference.

Allowing a patient's head to drop forward or sideways can also lead to unintended neck, shoulder, and spinal injuries. These injuries can be exacerbated during surgeries because unconscious (or heavily sedated) patients cannot protect themselves through reflexes or otherwise.

In the past, many cervical spine stabilization devices or techniques have been developed. Cervical spine stabilization devices arise from a spectrum of applications. On one end of the spectrum, neurosurgeons use Halo devices to stabilize the head and neck. However, some of these Halo devices use aggressive screws (pins) that are placed into the human skull.

On another end of the spectrum, physicians have used towels or pillows on either side of the cervical spine; often combined with some type of tape (duct tape or medical tape) to hold the "home made" apparatus together.

The most well-known cervical spine stabilization device is a standard neck brace (for example, the Aspen Collar). These are used by ambulances at the scene of an accident. They are also used in hospitals to maintain a safe neck position for patients who are at risk for cervical injury. The Aspen Collar, or equivalent collar, is used widely across the United States. However, collars are undesirable to use during surgery because they cover the front of the neck. This prevents surgeons from gaining access to the neck during surgical procedures. It also prevents anesthesiologists from having full access to the neck and airway during intubation for surgery.

Accordingly, it is an object of the present invention to provide a head stabilization device that can immobilize a patient's head while the patient is unconscious (or heavily sedated) and positioned on an operating table (or some other apparatus or surface) in an upright, sideways (tilted to the side), or upside down position, or in any other non-horizontal position, to reduce or eliminate soreness, strain, and/or injury to the neck, shoulder, or spine during surgery (or other medical procedure).

It is also an object of the present invention to provide a device that keeps the head, neck, and shoulders in the same relative positions, even with changes in position of an operating table, chair or some other apparatus.

It is another object of the present invention to provide a device that allows surgeons to have access the front of the neck during surgeries, and allows anesthesiologists to have full access to a patient's airway and neck during intubation for surgery.

It is a further object of the present invention to provide an inexpensive device that can be used for temporary prophylactic (preventative) use to prevent injury in a medical setting (for example, to prevent a patient's head from dropping forward when that patient is placed in an upright position during breast surgery).

It is still a further object of the present invention to provide a user-friendly device that utilizes simple straps, in contrast to invasive pins that are used in Halo devices or bulky pieces that must be secured together (such as in the Aspen Collar).

DISCLOSURE OF THE INVENTION

The above and other objects are preferably achieved by a device to stabilize a patient's head and neck when the patient is in a non-horizontal position. The device comprises a head support conformed to receive and retain the patient's head and neck; a flat platform having a top surface, a bottom surface, and sides, wherein the platform is freely slidable between stoppers in a direction substantially parallel to the patient's neck, and wherein the head support is attached to the top surface of the platform; two forehead straps attached to the sides of the platform, having first removable attachment surfaces for attaching each of the forehead straps to each other across the patient's forehead, wherein each of the forehead straps contains a chin strap extending from the forehead strap and having a second removable, attachment surface for attaching each of the chin straps, and wherein one of the chin straps has a cup for holding the patient's chin in place. The head support is also deep enough so that the patient's head contacts only the head support when the patient is unconscious and the forehead straps and the chin straps are fastened. Bed straps extending from the platform are also provided and configured to removably attach to an operating table. The device reduces strain, soreness, and injury to the patient's neck, shoulder, and spine when the patient is in a position that is not supine, but rather upright, sideways, upside down, or in any other non-horizontal position.

BRIEF DESCRIPTION OF THE DRAWINGS

FIG. 2 is a side elevational view of the invention from the right, showing a patient strapped into the device.

DETAILED DESCRIPTION OF THE PREFERRED EMBODIMENT

Figure 1:
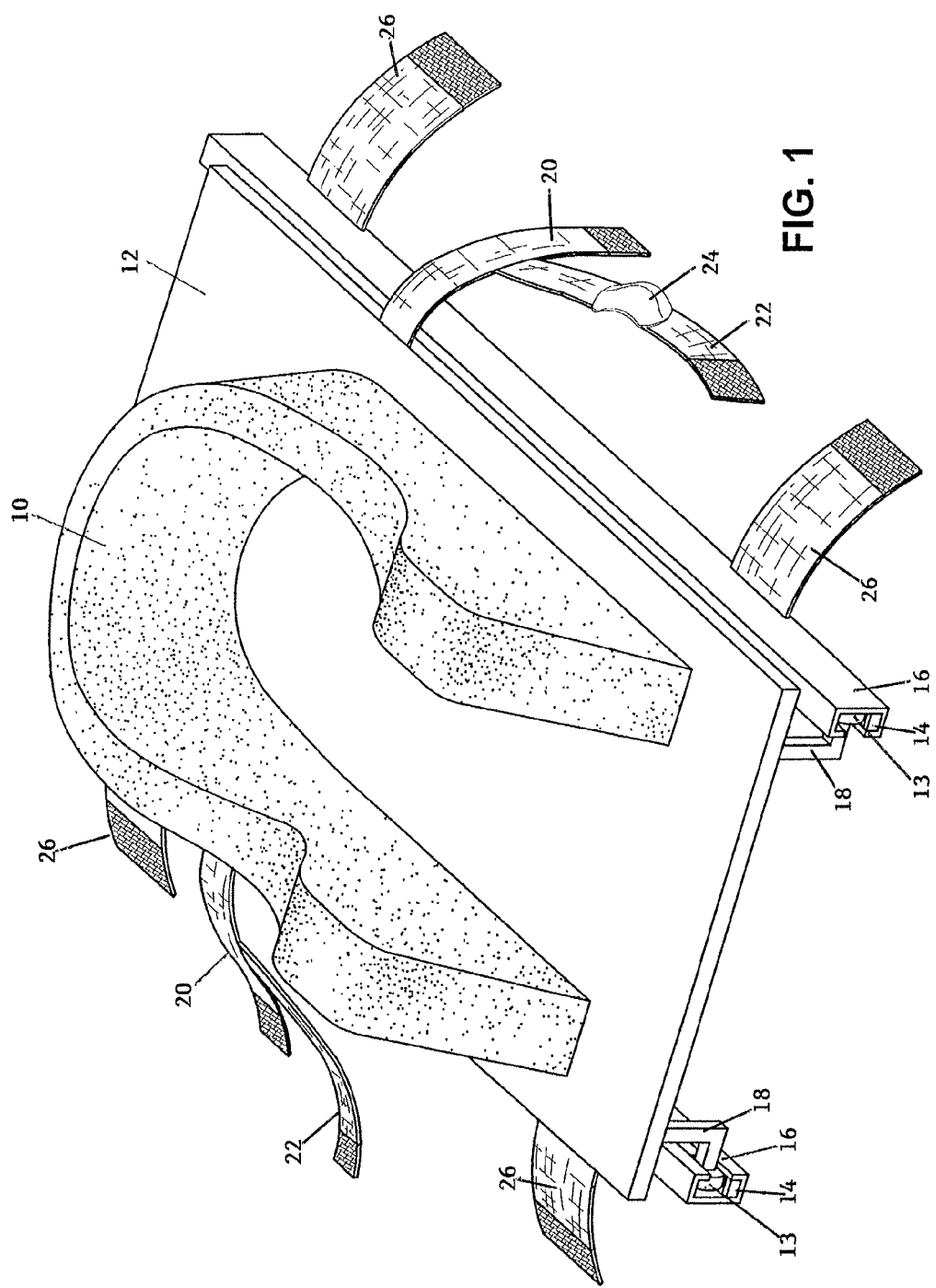
FIG. 1 is a perspective view of the presently preferred embodiment of the invention from the front top right thereof.

Referring to FIG. 1, the presently preferred embodiment of the present invention is a device comprising a head support 10, preferably made out of a firm pillow-like substance, such as foam, gel, or other similar material, shaped to receive and retain a patient's head and neck and secure them in a fixed position. The head support 10 is preferably attached, fastened, and/or fixed (in a permanent or removable manner) to the top surface of a platform 12 that can be attached, fastened, and/or fixed to a reclining or moveable operating table 28 (shown in FIG. 2) or other flat surface. The platform 12 can be made of any hard or firm material, such as plastic, polymer or metal, and its dimensions are preferably 8×10 inches, but can range from 4 to 14 inches in length and 4 to 14 inches in width. Preferably, the head support is the shape of an upside down U that is deep enough so that the patient's head only contacts the head support when the patient is unconscious and strapped in to the device (see below).

At least two tracks 16 are preferably located under the platform 12, preferably at least 4 inches apart, and optimally located at least 8 inches apart (but can vary depending on the size of the platform), for maximum stability of the platform 12 under the weight of a patient's body. Referring to FIG. 1, At least two sets of legs 18 are attached to the bottom surface of the platform 12. A first set is located at the head end of the platform closest to a patient's head, while a second set is located at the other end (the neck end of the platform) 12. The legs in each set are preferably located at least 5 inches apart. The legs extend downwardly from the platform and preferably are provided with caster wheels 13 (or another similar wheeled or non-wheeled device that allows for sliding) conformed to fit within the tracks to allow the device to slide along the tracks so that the platform 12 is slidably adjustable in relation to the operating table 28. A caster (or castor) wheel is an undriven, single, double, or compound wheel that is designed to be mounted to the bottom of a larger object so as to enable that object to be easily moved. Stoppers 14 located within the tracks prevent the caster wheels from sliding too far within the tracks. The stoppers are adjustable to accommodate different patient heights and sizes. The stoppers 14 are preferably placed along the tracks so that the entire device does not slide more than 4 inches from its original resting position. The freely sliding platform 12 along the operating table 28 or other flat surface allows the patient's head to move vertically when the patient (or patient's torso) is moved from a horizontal position to an upright position, or to any degree between 0-90 degrees from horizontal. This roller track system or equivalent sliding system accommodates changes in bed position. It keeps the head, neck, and shoulders in the same relative positions even with changes in tilt of the operating table or other apparatus. This prevents cervical injury patients who are under anesthesia and unable to voice any discomfort, pain, or other concerns.

Straps to secure the patient's forehead (forehead straps) 20 are preferably attached to each side of the platform 12 near the head end. The forehead straps on either side of the platform are preferably detachably attached to each other using any material that allows the forehead straps 20 to be securely fastened while remaining easily removable. For example, the forehead straps 20 could be fastened using a hook and loop (Velcro) fastener, or other similar fastener. The forehead straps 20 enable a patient's forehead to be secured to the head support 10 and platform 12 to minimize movement of the patient's head and neck during surgery. Each forehead strap also preferably has a chin strap 22. Like the forehead straps 20, each chin strap 22 preferably has a fastening mechanism that allows the chin straps to be removably fastened to each other. Preferably, one of the chin straps contains a cup for a patient's chin (chin cup) 24 that enables a patient's chin to be secured in the chin straps 22. Straps extending from the tracks (bed straps) 26 allow the invention to be secured to an operating table 28 or other surface. The bed straps 26 are also preferably fastened to an operating table in a removable fashion, using such material as hook and loop fasteners.

Referring to FIG. 2, shown is the presently preferred embodiment of the invention with a patient securely fastened into it through the use of the forehead straps 20, chin straps 22, and chin cup 24. The invention is securely fastened to the operating table 28 through the bed straps 26.

If a patient is in a sideways or upside down position, the patient's legs would also need to be secured to the table through straps or some other similar device (not shown).

INDUSTRIAL APPLICABILITY

The presently preferred embodiment of the invention is a head stabilization device that can be used any time is desired to stabilize a patient's head when the patient is upright, sideways (tilted to the side), or in an upside down position, or in any other non-horizontal position.

We claim:

1. A device to stabilize a patient's head, neck and shoulders when said patient is in a non-horizontal position comprising:
   a head support conformed to receive, retain and support said patient's head and neck in a fixed position in alignment with each other;
   a flat platform having a top surface, a bottom surface, sides, and legs extending downwardly from said bottom surface;
   wheels attached to said legs;
   tracks mounted on said wheels;
   wherein said platform is freely slidable between stoppers within said tracks in a direction substantially parallel to said patient's neck, and wherein said head support is attached to said top surface of said platform;
   two forehead straps attached to said sides of said platform, having first removable attachment surfaces for attaching each of said forehead straps to each other across said patient's forehead,
   wherein each of said forehead straps contains a chin strap extending from said forehead strap and having a second removable, attachment surface for attaching each of said chin straps, and
   wherein one of said chin straps has a cup for holding said patient's chin in place;
   wherein said head support is deep enough so that said patient's head and neck contact only said head support, said forehead straps and said chin straps, when said patient is unconscious and said forehead straps and said chin straps are fastened;

bed straps extending from said tracks configured to removably and directly strap said tracks to an operating table, whereby said device is attached to said operating table;

wherein said patient's head and neck freely slide only in a direction that is substantially parallel to said patient's neck wherein said patient's head and neck remain in the same relative positions with respect to said patient's shoulders while said operating table is being tilted; and whereby said device reduces strain, soreness, and injury to said patient's neck, shoulder, and spine.

2. A device to stabilize a patient's head, neck and shoulders when said patient is in a non-horizontal position comprising:

a head su ort conformed to receive retain and su ort said patient's head and neck in a fixed position in alignment with each other;

a flat platform having a top surface, a bottom surface, and sides;

legs extending downwardly from said platform;

wheels attached to said legs;

tracks mounted on said wheels;

wherein said platform is freely slidable between stoppers within said tracks in a direction substantial parallel to said patient's neck and wherein said head support is attached to said to surface of said platform;

two forehead straps attached to said sides of said platform, having first removable attachment surfaces for attaching each of said forehead straps to each other across said patient's forehead, wherein each of said forehead straps contains a chin strap extending from said forehead strap and having a second removable, attachment surface for attaching each of said chin straps, and wherein one of said chin straps has a cup for holding said patient's chin in place;

wherein said head support is deep enough so that said patient's head and neck contact only said head support, said forehead straps and said chin straps, when said patient is unconscious and said forehead straps and said chin straps are fastened;

bed straps extending from said tracks configured to removably and directly strap said tracks to an operating table, whereby said device is attached to said operating table; and whereby said device reduces strain, soreness, and injury to said patient's neck, shoulder, and spine.

3. A device to stabilize a patient's head, neck and shoulders when said patient is in a non-horizontal position comprising:

a head support conformed to receive, retain and support said patient's head and neck in a fixed position in alignment with each other;

a flat platform having a top surface, a bottom surface, and sides;

legs extending downwardly from said platform containing wheels mounted within tracks;

wherein said s platform is freely slidable between stoppers within said tracks in a direction substantially parallel to said patient's neck, and wherein said head support is attached to said top surface of said platform;

two forehead straps attached to said sides of said platform, having first removable attachment surfaces for attaching each of said forehead straps to each other across said patient's forehead, wherein each of said forehead straps contains a chin strap extending from said forehead strap and having a second removable, attachment surface for attaching each of said chin straps, and wherein one of said chin straps has a cup for holding said patient's chin in place;

wherein said head support is deep enough so that said patient's head and neck contact only said head support, said forehead straps and said chin straps, when said patient is unconscious and said forehead straps and said chin straps are fastened;

bed straps extending from said tracks configured to removably and directly strap said tracks to an operating table, whereby said device is attached to said operating table;

wherein said patient's head and neck freely slide only in a direction that is substantially parallel to said patient's neck wherein said patient's head and neck remain in the same relative positions with respect to said patient's shoulders while said operating table is being tilted; and whereby said device reduces strain, soreness, and injury to said patient's neck, shoulder, and spine.

* * * * *